United States Patent [19]

Chalmers

[11] Patent Number: 5,643,589
[45] Date of Patent: Jul. 1, 1997

[54] DESICCANT FORMULATED FOR TREATING WOUNDS OR LESIONS

[76] Inventor: Susanna Elizabeth Chalmers, 28 Lobelia Street, Heldervue Somerset West Cape Province, South Africa, 7130

[21] Appl. No.: 163,454

[22] Filed: Dec. 6, 1993

[30] Foreign Application Priority Data

Dec. 7, 1992 [ZA] South Africa ............... 92/9459

[51] Int. Cl.$^6$ ............... H01N 25/34; H01N 25/08
[52] U.S. Cl. ............... 424/404; 424/402; 424/409; 424/411; 424/443
[58] Field of Search ............... 424/678, 720, 424/697, 445, 402, 404, 409, 443, 411, 447

[56] References Cited

U.S. PATENT DOCUMENTS

| | | | |
|---|---|---|---|
| 3,729,555 | 4/1973 | Gradnik | 514/199 |
| 3,984,540 | 10/1976 | Willard, Sr. | 424/678 |
| 4,524,064 | 6/1985 | Nambu | 424/81 |
| 4,608,044 | 8/1986 | Nordqvist et al. | 604/290 |
| 4,772,627 | 9/1988 | Matsui et al. | |
| 4,803,066 | 2/1989 | Edwards | 424/132 |
| 5,204,110 | 4/1993 | Cartmell et al. | 424/443 |
| 5,225,197 | 7/1993 | Bolt et al. | 424/440 |

FOREIGN PATENT DOCUMENTS

| | | |
|---|---|---|
| A 44599/93 | 2/1994 | Australia . |
| 0 137 743 | 4/1985 | European Pat. Off. . |
| 2 669 530 | 11/1990 | France . |
| 2 129 430 | 6/1971 | Germany . |
| 23 31 097 | 1/1975 | Germany . |
| 1121902 | 7/1968 | United Kingdom . |
| 1454055 | 10/1976 | United Kingdom . |
| 1 522 770 | 8/1978 | United Kingdom . |
| WO 91/06289 | 5/1991 | WIPO . |

OTHER PUBLICATIONS

Red List, 1991, 91 0388, European Patent Office, English translation.

*Primary Examiner*—Thurman K. Page
*Assistant Examiner*—Sharon Howard
*Attorney, Agent, or Firm*—Pennie & Edmonds LLP

[57] ABSTRACT

This invention relates to a pharmaceutical composition for use in treating an abnormal skin condition, such as a wound, a burn or a blister, in an animal or human. The pharmaceutical composition has an antiseptic or antimicrobial agent and a desiccant for adsorbing moisture or liquid, in and around the area of the abnormal skin, in a form such that the adsorbed moisture or liquid is not readily available to the skin.

15 Claims, 1 Drawing Sheet

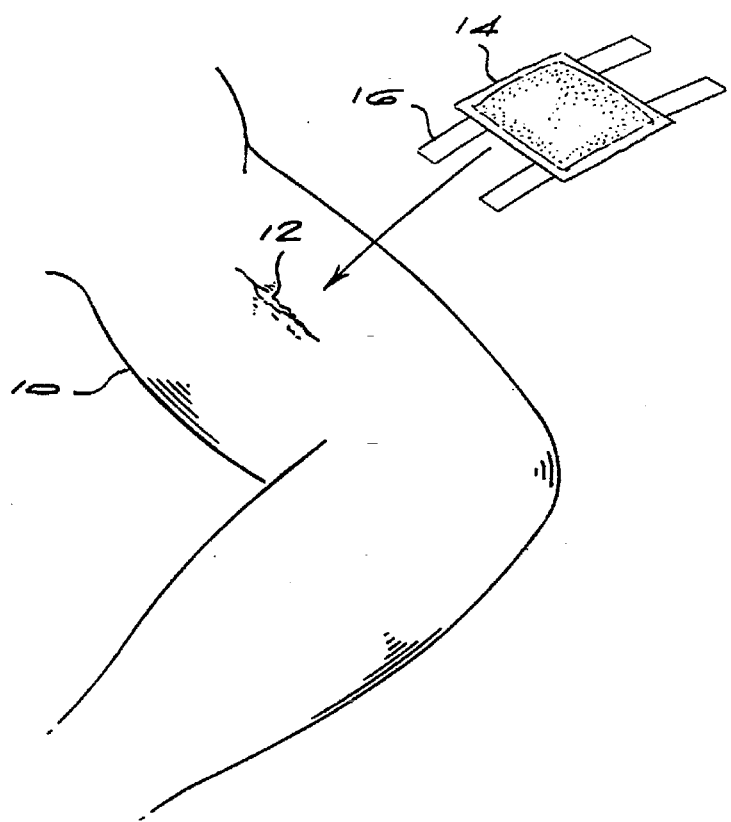
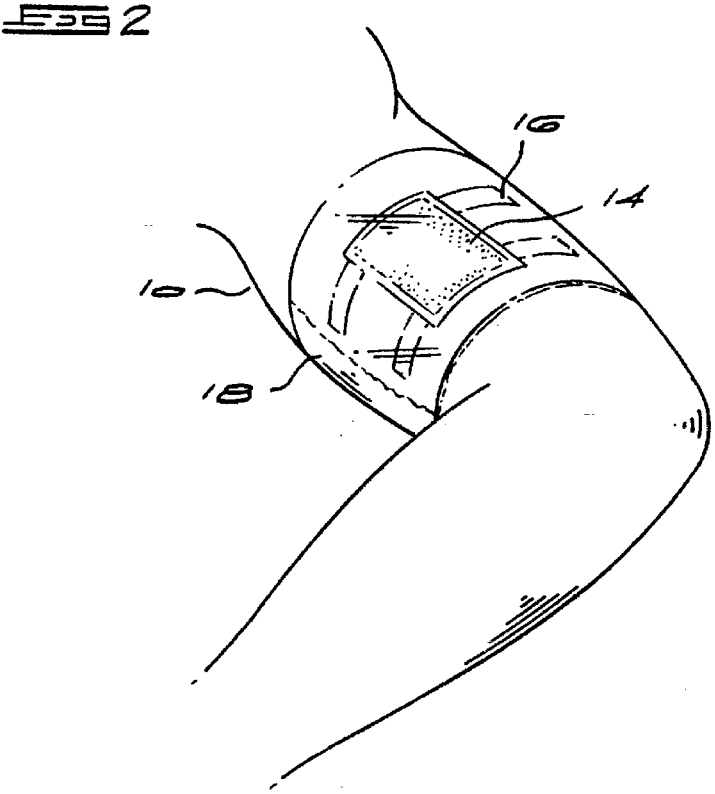

DESICCANT FORMULATED FOR TREATING WOUNDS OR LESIONS

BACKGROUND OF THE INVENTION

This invention relates to a pharmaceutical composition for treating abnormal skin conditions in humans or animals.

Wounds, burns or blisters can cause great pain to patients. Further, if such conditions are not treated properly, the skin may not heal properly and the condition may turn septic causing further complications.

It is an object of this invention to suggest a pharmaceutical composition which will assist the healing process and alleviate the aforesaid problems.

SUMMARY OF THE INVENTION

According to the invention there is provided a pharmaceutical composition, for use in treating an abnormal skin condition in an animal or human, comprising:

(a) an antiseptic or antimicrobial agent; and (b) a desiccant for adsorbing moisture or liquid, in and around the area of the abnormal skin, in a form such that the adsorbed moisture or liquid is not readily available to the skin.

Preferably, the desiccant is silica gel or anhydrous calcium chloride. More preferably the desiccant is silica gel.

Preferably, the antiseptic agent is a hyperosmotic agent which operatively raises the osmotic pressure in the environment around any bacteria arising from the abnormal skin condition, thereby inhibiting or killing the bacteria. Typically, the hyperosmotic agent is an inorganic salt. Preferably, the inorganic salt is sodium chloride, ammonium chloride or magnesium sulphate. More preferably the inorganic salt is sodium chloride.

The antimicrobial agent may be an antibacterial agent such as silver oxide, iodine, a sulphonamide, penicillin or a tetracycline.

Typically, the abnormal skin condition is a skin lesion, such as a wound, a blister or a burn.

According to another aspect of the invention there is provided a dressing, for use in treating an abnormal skin condition in an animal or human, containing a pharmaceutical composition as summarised above. Preferably, the dressing is a liquid or moisture permeable sachet and the pharmaceutical composition is contained therein. The sachet may include adhesive strips for adhering the sachet to human or animal skin.

According to another aspect of the invention there is provided a kit, for dressing an abnormal skin condition in an animal or human, comprising a dressing as summarised above which, in use, is placed over the abnormal skin, and a liquid or moisture impermeable sheet which, in use, is wrapped over the sachet. The sheet may be formed integral with, or separate from, the sachet.

According to another aspect of the invention there is provided the use of a pharmaceutical composition as summarised above in the manufacture of a medicament useful in treating an open or broken skin condition in an animal or human.

BRIEF DESCRIPTION OF THE DRAWINGS

The invention will now be described in more detail, by way of example only, with reference to the accompanying drawings in which:

FIG. 1 shows a sachet according to the invention, and part of a human arm having a wound inflicted thereon; and FIG. 2 shows the sachet of FIG. 1 applied to the human arm.

DESCRIPTION OF EMBODIMENTS

FIG. 1 shows a human arm 10 which has a wound 12 inflicted thereon. There is also shown a sachet 14 according to the invention having adhesive strips 16 attached thereto.

The sachet 14 is sealed along its edges and is made of a moisture and liquid permeable material. A suitable material for the sachet which is currently available is marketed under the trade name "Lutrisil". The adhesive strips 16 are suitably manufactured to be removably attachable to human skin.

The sachet 14 has a pharmaceutical composition according to the invention located therein.

The following words have the definitions as set out hereunder for the purposes of this specification. The definitions arise in part from Churchill's Medical Dictionary, Second Edition, published by Roshe Lexicon Medizine.

Antiseptic: Pertaining to, or capable of, effecting antisepsis. A substance capable of inhibiting or killing infectious agents, usually on a body surface.

Antimicrobial: Acting to kill or inhibit growth and multiplication of microbes. An agent which kills or inhibits the growth and multiplication of microbes. The term includes antibacterial and antifungal agents.

Abnormal skin condition: This term includes within its scope any type of superficial wound or skin lesion such as a blister, a burn, or a wound, open or closed, septic or aseptic. The term also includes surgical wounds.

The pharmaceutical composition according to the invention includes an antiseptic or antimicrobial agent and a desiccant. The desiccant is specifically of the type which adsorbs moisture or liquid in and around the area of an abnormal skin condition in an animal or human, such as a wound, a blister or burn. The adsorbed moisture of liquid is held by the desiccant in a form which is not readily available to the wound.

Prior art pharmaceutical compositions contain antimicrobial agents and water adsorbing agents such as ethyl cellulose, gelatine and agar. The disadvantage of water adsorbing agents is that the water which they adsorb is still available to the wound. An equilibrium is typically reached where no more water can be adsorbed and the remaining water merely remains in the wound creating an environment which is ideal for bacterial growth. Even the adsorbent which holds the adsorbed water is "wet" which again creates an environment which is ideal for bacterial growth. However, in the pharmaceutical composition of the present invention, a desiccant is used which substantially removes moisture or liquid from the wound, and from the atmosphere in and around the wound, by absorption, and which subsequently holds the liquid in a form that is not readily available to the wound again. Anhydrous calcium chloride can hold water in the form of crystallization which is not available again to the wound. A particularly suitable desiccant for use in the pharmaceutical composition of the invention is silica gel. Silica gel is able to hold water particularly effectively and in fact the only way to remove adsorbed water from the silica gel is to heat it to 100° C. By using such a desiccant, liquid is actively removed from the wound, and from the atmosphere around the wound, thereby keeping the wound substantially dry at all times.

The antiseptic or antimicrobial agent may be inorganic or organic. Although organic antimicrobials and antiseptics are included within the scope of the pharmaceutical composition of the invention, it has been found that such substances may cause allergies in patients sensitive to these chemicals, and are also not relatively cost effective. Preferably, the antimicrobial agent or antiseptic agent is an inorganic salt. The antiseptic or antimicrobial agent may be of the type which acts directly on the bacteria, such as an antibacterial or antifungal agent, or they may be of the type which raise the osmotic pressure around the bacteria so as to kill or inhibit the bacteria, commonly known as hyperosmotic agents. Hyperosmotic agents are preferred in the pharmaceutical composition of the invention. Sodium chloride, ammonium chloride and magnesium sulphate have been found to be effective hyperosmotic agents. Sodium chloride has proved to be particularly effective in inhibiting bacterial growth and is also cost effective. Iodine, silver oxide, a sulphonamide, penicillin and a tetracycline are examples of antibacterial agents.

A typical example of a pharmaceutical composition according to the invention comprises 20 grams of sodium chloride and 80 grams of silica gel.

FIG. 2 illustrates how the sachet 14 of FIG. 1 is applied to the wound 12. The sachet 14 is located over the wound 12 and the adhesive strips 16 are applied to the skin of the arm 10. The liquid and exudate, including any bacteria, of the wound pass through the permeable walls of the sachet 14. The desiccant adsorbs the liquid such that it cannot pass back through the walls of the sachet 14 onto the wound. The antiseptic or antimicrobial agents kill or inhibit the bacteria inside the sachet 14. The advantage of using a sachet is that the desiccant and antiseptic/antimicrobial agents do not come into physical contact with the skin. This obviates any possible skin irritation problems which may occur with direct skin contact with such chemicals. Further, the adsorbed liquid and inhibited/killed bacteria are kept within the walls of the sachet 14 and do not come into physical contact again with the skin. A sheet 18 is then wrapped around the arm 10 and over the sachet 14. The sheet 10 is made of a liquid and moisture impermeable material, such as polyethylene. The sheet of polyethylene prevents atmospheric moisture from reaching the sachet. The sheet 18 may be separate of the sachet 14, or may be integrally formed with the sachet 14. Typically, the sachet is replaced at regular intervals, for example every 4 to 6 hours, depending on the state of the wound. The sachet 14 and sheet 18 are conveniently provided in the form of a kit. The kit comprises the sheet 18 and sachet 14 and both are typically placed in a moisture proof polymeric plastic bag to maintain dryness and sterility. The entire product may be sterilized by a suitable means, for example gramma irradiation.

I claim:

1. A dressing for use in treating an abnormal skin condition in an animal or human, comprising a liquid permeable sachet containing a dry topical pharmaceutical composition, the topical pharmaceutical composition comprising:

(a) an antiseptic or antimicrobial agent; and (b) a desiccant for adsorbing moisture or liquid in and around the area of the abnormal skin condition through the liquid permeable sachet so that the adsorbed moisture or liquid is not readily available to the skin.

2. The dressing according to claim 1 wherein the desiccant is selected from the group consisting of silica gel and anhydrous calcium chloride.

3. The dressing according to claim 1 wherein the desiccant is silica gel.

4. The dressing according to claim 1 wherein the antiseptic or antimicrobial agent is a hyperosmotic agent which operatively raises the osmotic pressure in the environment around any bacteria arising from the abnormal skin condition, thereby inhibiting or killing the bacteria.

5. The dressing according to claim 1 wherein the antiseptic or antimicrobial agent is a hyperosmotic agent which includes an inorganic salt.

6. The dressing according to claim 1 wherein the antiseptic or antimicrobial agent is selected from the group consisting of sodium chloride, ammonium chloride and magnesium sulphate.

7. The dressing according to claim 1 wherein the antiseptic or antimicrobial agent is sodium chloride.

8. The dressing according to claim 1 wherein the antiseptic or antimicrobial agent is an antibacterial agent.

9. The dressing according to claim 1 wherein the antiseptic or antimicrobial agent is silver oxide, iodine, a sulphonamide, penicillin or a tetracycline.

10. The dressing according to claim 1 wherein the abnormal skin condition is a skin lesion.

11. The dressing according to claim 1 wherein the abnormal skin condition is a wound, a burn or a blister.

12. A method of treating an abnormal skin condition in an animal or human including the step of applying to the abnormal skin condition a dressing comprising a liquid permeable sachet containing a dry topical pharmaceutical composition, the topical pharmaceutical composition comprising:

(a) an antiseptic or antimicrobial agent; and (b) a desiccant for adsorbing moisture or liquid, in and around the area of the abnormal skin condition so that the adsorbed moisture or liquid is not readily available to the skin.

13. The dressing of claim 1 wherein the contents of said sachet consists essentially of a major portion of said desiccant and a minor portion of said antiseptic or antimicrobial agent.

14. The dressing of claim 13 wherein the contents of said sachet consists essentially of about 80% desiccant and about 20% antiseptic or antimicrobial agent.

15. The dressing of claim 14 wherein the contents of said sachet consists essentially of about 80% by weight silica gel and about 20% by weight sodium chloride.

* * * * *